(12) United States Patent
Tan

(10) Patent No.: US 9,216,190 B2
(45) Date of Patent: Dec. 22, 2015

(54) ANALGESIC METHOD

(71) Applicant: I-SHOU UNIVERSITY, Kaohsiung (TW)

(72) Inventor: Ping-Heng Tan, Kaohsiung (TW)

(73) Assignee: I-SHOU UNIVERSITY, Kaohsiung (TW)

( * ) Notice: Subject to any disclaimer, the term of this patent is extended or adjusted under 35 U.S.C. 154(b) by 0 days.

(21) Appl. No.: 14/057,935

(22) Filed: Oct. 18, 2013

(65) Prior Publication Data

US 2014/0039040 A1 Feb. 6, 2014

Related U.S. Application Data

(62) Division of application No. 13/568,736, filed on Aug. 7, 2012, now abandoned.

(30) Foreign Application Priority Data

Jun. 11, 2012 (TW) .............................. 101120890 A

(51) Int. Cl.
*A61K 31/713* (2006.01)
*A61K 9/00* (2006.01)

(52) U.S. Cl.
CPC .............. *A61K 31/713* (2013.01); *A61K 9/0019* (2013.01)

(58) Field of Classification Search
None
See application file for complete search history.

(56) References Cited

U.S. PATENT DOCUMENTS

| 7,807,815 | B2 | 10/2010 | MacLachlan et al. |
| 7,863,436 | B2 | 1/2011 | Milner |
| 2004/0082914 | A1* | 4/2004 | Hooper ..................... 604/164.01 |
| 2006/0199779 | A1* | 9/2006 | Goregaoker et al. ........... 514/44 |
| 2006/0223742 | A1 | 10/2006 | Salazar |
| 2006/0241074 | A1 | 10/2006 | Woolf et al. |
| 2007/0105806 | A1* | 5/2007 | Sah et al. ........................ 514/44 |
| 2011/0021606 | A1 | 1/2011 | Barik |
| 2012/0034248 | A1 | 2/2012 | Kandimalla et al. |
| 2012/0328644 | A1 | 12/2012 | Li et al. |

OTHER PUBLICATIONS

Jiang, et al., "Analgesic effect of interferon-alpha via mu opioid receptor in the rat", Neurochemistry International 36, 2000, pp. 193-196.
Dafny, et al, "Interferon and the central nervous system", European Journal of Pharmacology 523, 2005, pp. 1-15.
Wang, et al.,"μ but not o and K-opioid receptor mediates the nucleus submedius interferon-a-evoked antinociception in the rat", Neuroscience Letters 397, 2006, pp. 254-258.
Tan, et al, "Short small-interfering RNAs produce interferon-a-mediated analgesia", British Journal of Anaesthesia, Feb. 3, 2012, pp. 1-8.

* cited by examiner

*Primary Examiner* — Tracy Vivlemore
(74) *Attorney, Agent, or Firm* — Muncy, Geissler, Olds & Lowe, P.C.

(57) ABSTRACT

An analgesic medication includes an oligonucleotide being a double strand RNA comprising 18 to 70 base pairs, and a pharmaceutical acceptable vehicle for delivering the said oligonucleotide into cells, wherein a dosage of the oligonucleotide in the analgesic is 50 μg to 200 μg/kg per time, and the pharmaceutical acceptable vehicle is selected from a group of polyethyleneimine, lipofectamine and iFect.

14 Claims, 4 Drawing Sheets

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Non-targeting siRNA

<400> SEQUENCE: 1
uagcgacuaa acacaucaau u                                               21

<210> SEQ ID NO 2
<211> LENGTH: 21
<212> TYPE: RNA
<213> ORGANISM: Artificial Sequence
<220> FEATURE:
<223> OTHER INFORMATION: Non-targeting siRNA

<400> SEQUENCE: 2
uugauguguu uagucgcuau u                                               21

<210> SEQ ID NO 3
<211> LENGTH: 19
<212> TYPE: RNA
<213> ORGANISM: Artificial Sequence
<220> FEATURE:
<223> OTHER INFORMATION: GU-rich siRNA

<400> SEQUENCE: 3
uugauguguu uagucgcua                                                  19
```

```
<210> SEQ ID NO 4
<211> LENGTH: 19
<212> TYPE: RNA
<213> ORGANISM: Artificial Sequence
<220> FEATURE:
<223> OTHER INFORMATION: GU-rich siRNA

<400> SEQUENCE: 4
uagcgacuaa acacaucaa                                              19
```

ANALGESIC METHOD

This is a divisional application of U.S. patent application Ser. No. 13/568,736 filed on Aug. 7, 2012.

BACKGROUND OF THE INVENTION

1. Field of the Invention

The present invention generally relates to an analgesic medication, and, more particularly, to an analgesic medication comprising oligonucleotides capable of inducing interferon response and analgesic effects.

2. Description of the Related Art

Interferons (IFNs) are proteins made and released by host cells in response to viruses or other pathogens infection, which can trigger protective defenses of immune system, interfering replication of virus (or other pathogens) and proliferation of host cell, so as to reduce or avoid adjacent host cells being further infected by virus or pathogens.

Interferons found in human body are typically divided into two classes: class I, primary comprising interferon-α and interferon-β (also comprising interferon-ω, interferon-τ, interferon-γ, interferon-κ, and interferon-ε); and class II, comprising interferon-γ. Recent studies showed that interferon-γ is produced by astrocyte in the central nervous system (CNS) and enhanced neuropathic pain by stimulation of interferon-γ receptors specifically expressed in spinal microglia. Yet, the class I interferons are produced by leukocytes and mainly involved in innate immune response against pathogen infection. Wherein, interferon-α, as an important part in stimulation of both macrophages and natural killer cells is apt to against viral infection, to boost immunity, as well as to inhibit tumor growth.

In conventional art, the interferon-α has been now industrial produced via biotechnological engineering, and widely applied to various medical fields, suppressing viral infection and tumor progressing. Moreover, the interferon-α has further used in clinical analgesia, providing reversible analgesic effects in peripheral and central nervous system (Jiang et al., Analgesic effect of interferon-alpha via mu opioid receptor in the rat. 2000. Neurochemistry International 36, 193-196) though g-opioid receptor (Wang et al., μ-but not δ- and κ-opioid receptor mediates the nucleus submedius interferon-α-evoked antinociception in the rat. 2006. Neuroscience Letters 397, 254-258).

However, a long-term use of interferon-α may develop plenty side effects, such as fever, chili, muscle and bone pains, insomnia, poor appetites, weight loss, and fatigue. Although those side effects will not result in serious damages or complications, people still suffer from uncomfortableness and inconvenience in daily life. Under such circumstance, industrial produced interferon-α is limited in practical use, especially in a development of analgesic medication or analgesic treatment.

SUMMARY OF THE INVENTION

It is therefore the objective of this invention to provide an analgesic medication, which can induce α-interferon response, to achieve analgesic effects or pain relief without leading to the said side effects.

It is therefore the further objective of this invention to provide an analgesic medication, which can be applied to clinical analgesia for pain relief.

One embodiment of the present invention discloses an analgesic medication comprising: an oligonucleotide being a double strand RNA comprising 18 to 70 base pairs, and a pharmaceutical acceptable vehicle for delivering the said oligonucleotide into cells, wherein a dosage of the oligonucleotide in the analgesic is 50 μg to 200 μg/per kg/each time, and the pharmaceutical acceptable vehicle is selected from a group of polyethyleneimine, lipofectamine and iFect.

In the preferred form shown, the analgesic medication comprises the said oligonucleotide, with more than 40% bases therein being uracil and guanine, and having sequences set forth in SEQ ID NO: 1 and 2, or SEQ ID NO: 3 and 4.

In the preferred form shown, the analgesic medication comprises the said oligonucleotide and the pharmaceutical acceptable vehicle mixed in a ratio of 1 μg:0.184 μl.

In the preferred form shown, the analgesic medication comprises the said oligonucleotide, being synthesized chemically, or expressed by a viral system, wherein the viral system is a cytomegalomavirus system, or a lentiviral system, with the oligonucleotide being small interfering RNA, short hairpin RNA, or microRNA.

In the preferred form shown, the analgesic medication is delivered to an individual via intrathecal injection, which is used for systemic analgesia or pain relief, as well as local analgesia on lumbar vertebra, extremity or lower body.

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein.

Figure 1:
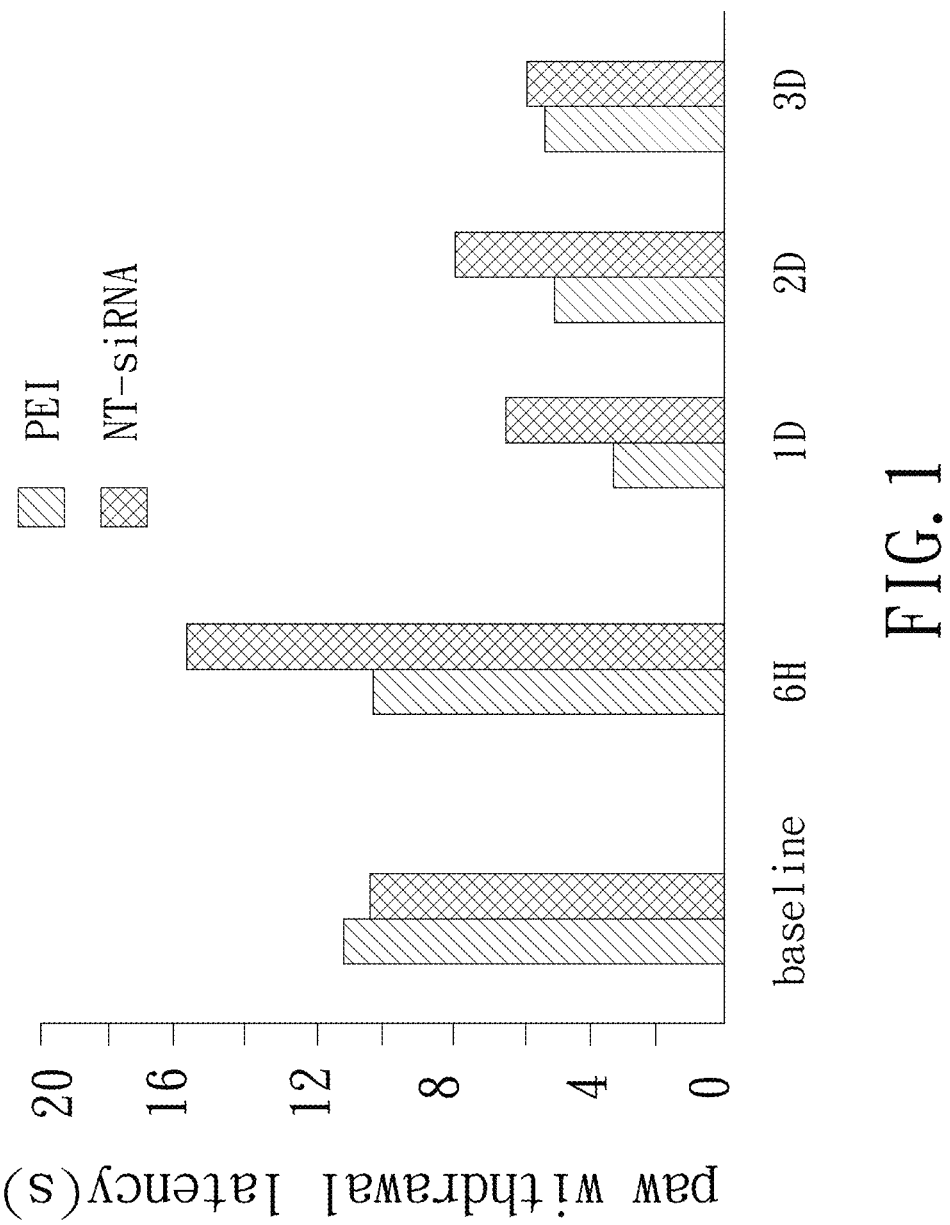
FIG. 1 is a bar chart illustrating paw withdrawal latency of SD rats in each group.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the

DETAILED DESCRIPTION OF THE INVENTION

A preferable embodiment of the present invention relates to an analgesic medication comprising an isolated oligonucleotide. The oligonucleotide is a double strand RNA comprising nucleotide sequences that is or is not homologous to organism genes. The oligonucleotide has 18 to 70 base pairs, preferably 18 to 25 base pairs, or 40 to 60 base pairs, to induce interferon-α response in hosts. The oligonucleotide is combined with a pharmaceutical acceptable vehicle, such as polyethyleneimine (PEI), lipofectamine and iFect, preferably with PEI and in a ratio of 0.18 μl PEI:1 μg oligonucleotide, so that the oligonucleotide can be successfully delivered to cells in central nervous system.

When delivering the said oligonucleotide in an individual (a rat or human body), the said oligonucleotide can induce interferon-α response, to achieve reversible analgesic effects in central or peripheral nervous systems via μ-opioid receptor.

Furthermore, in a preferable embodiment of the present invention, a dosage of the said oligonucleotide in the analgesic medication is more than 50 μg/per kg/each time, preferably 50 μg to 200 μg/kg, for achieving better analgesic effects. Also, the said oligonucleotide in the preferable embodiment comprises a high ratio of uracil and guanine, preferably more than 40% in comparison with total bases, in order to effectively induce interferon-α response, and to achieve analgesic effects in central nervous system.

With reference to TABLE 1, the analgesic medication of the preferable embodiment preferably comprises the oligonucleotide that has a sequence as set forth in SEQ ID NO. 1 and 2, or 3 and 4. When delivering the oligonucleotide of the preferable embodiment of the present invention in an individual (a rat or human body), the oligonucleotide can effectively induce interferon-α response, then to achieve reversible analgesic effects in central or peripheral nervous systems via μ-opioid receptor. It is proved that, the analgesic medication comprising the oligonucleotide as shown in TABLE 1 has the said benefits, and therefore, the analgesic medication of the present invention is sufficient to be further applied to clinical medicine for systemic analgesia, particularly for lumbar vertebra, extremity or other parts of lower body.

The olignonucleotides of the preferable embodiment in the present invention can be designed as small interfering RNAs (siRNAs), small hairpin RNAs (shRNAs), or microRNAs, and be synthesized both recombinantly in appropriate vector systems, as well as chemically. Suitably, the vector systems can be eukaryote vector systems, for example yeasts; prokaryotic vector systems, for example E. coli; viral vector systems or others, that are well known to person in the art. Yet, the olignonucleotides can be chemically synthesized by numerous standardized methods, including designing the olignonucleotides, with the olignonucleotides comprising 18 to 70 base pairs and having more than 40% of uracil and guanine in comparison with total bases, and synthesizing the oligonucleotides by Dharmacon Research Incorporation (Lafayette Co., USA).

The analgesic medication of the preferable embodiment in the present invention are delivered to cerebrospinal fluid of an individual via intrathecal (spinal) injection, preferably between L5 and L6 of the spinal column. The analgesic medication comprises more than 50 μg/kg of the oligonucleotide, 50 μg to 200 μg/kg in preferable; and the pharmaceutical acceptable vehicle for delivering the said oligonucleotide into cells. The analgesic medication can be further manufactured into a complex in a type for easy injecting, solution and injection for example, by combining with pharmaceutical acceptable excipients, salts or nutrients. The analgesic medication of the present invention is apt to be used as a pain killer or analgesic drug, and which is capable of being applied to systemic analgesia in clinical medicine, in particular on lumbar vertebra, extremity or other parts of lower body.

In the following paragraphs, benefits of the analgesic medication of the present invention is demonstrated and proved.

In experiments, several adult male Sprague-Dawley rats (SD rats; 200 g to 260 g) are prepared and housed to maintain physiological functions of the said SD rats. Next, the oligonucleotides, labeled as A and B comprising sequences set forth in TABLE 1 are synthesized, purified, and annealed by Dharmacon Research Incorporation (Lafayette Co., USA) respectively. Also, a PEI solution is prepared by dissolving the PEI in 5% glucose, wherein 0.18 μl of the PEI solution is mixed with per microgram of the oligonucleotide in the experiment of the present invention.

With reference to TABLE 2, the said SD rats are randomly assigned into several groups and carried out two injections, with a first injection thereof being performed by intrathecally injecting 40 μl saline, 1.8 μl the PEI solution, 10 μg the oligonucleotide A, mixtures comprising various dosages of the oligonucleotide A and the PEI solution, and a mixture comprising the oligonucleotide B and the PEI solution to the said seven groups respectively, in a use of a 30 G needle between L5 and L6 of the spinal column. Moreover, a second injection is performed one day after the first injection, by subcutaneously injecting 100 μl complete Freund's adjuvant (CFA) on a hind paw of the SD rats of each group. Then, mechanical allodynia is tested in six hours (6H) and one day (1 D) after the second injection.

TABLE 1

Oligonucleotides in the Preferable Embodiment

| A | 5'-UAGCGACUAAACACAUCAAUU-3' | (SEQ ID NO. 1) |
|---|---|---|
| (Non-targeting siRNA) | 3'-UUAUCGCUGAUUUGUGUAGUU-5' | (SEQ ID NO. 2) |
| B | 5'-UUGAUGUGUUUAGUCGCUA-3' | (SEQ ID NO. 3) |
| (GU-rich siRNA) | 3'-AACUACACAAAUCAGCGAU-5' | (SEQ ID NO. 4) |

TABLE 2

Assignment of the Said Seven Groups

| Groups | Saline | PEI | A (10 μg) | A + PEI (5 μg) | A + PEI (10 μg) | A + PEI (20 μg) | B + PEI (10 μg) |
| --- | --- | --- | --- | --- | --- | --- | --- |
| Baseline | 12.28 (3.35) | 14.76 (0.62) | 14.25 (1.85) | 14.82 (0.40) | 14.08 (1.8) | 13.81 (1.85) | 13.48 (2.73) |
| CFA 6 H | 2.93 (1.35) | 3.07 (2.06) | 3.06 (1.41) | 3.13 (1.46) | 2.82 (1.21) | 7.8 (3.73) | 5.12 (1.52) |
| CFA 1 D | 3.47 (1.73) | 2.44 (1.65) | 5.81 (3.52) | 3.26 (2.34) | 9.33 (3.22) | 14.12 (2.93) | 12.1 (2.93) |

Data in TABLE 2 indicate that, CFA-induced allodynia is attenuated by the analgesic medication of the preferable embodiment of present invention (whatever comprising the oligonucleotide A or B) delivered intrathecally and dose-dependently, and however, solely injecting of the oligonucleotides or PEI solution will not block the CFA-induced allodynia. Accordingly, it is believed the analgesic medication of the present invention truly has benefits to achieve analgesic effects.

Referring to FIG. 1, another two groups of SD rats are prepared and carried out two injections, similarly with a first injection thereof being performed by intrathecally injecting 1.8 μl the PEI solution or a mixture comprising 10 μg the oligonucleotide A and the PEI solution, and with a second injection thereof being performed by subcutaneously injecting 100 μl CFA on a hind paw of the SD rats of each group. After that, paw withdrawal latency of the SD rats in each group are tested in six hours (6H), one day (1 D), two days (2 D) and three days (3 D) after the second injection.

In FIG. 1, it is indicated that CFA-induced heat hypersensitivity is also attenuated by the analgesic medication of present invention delivered intrathecally.

Figure 2:
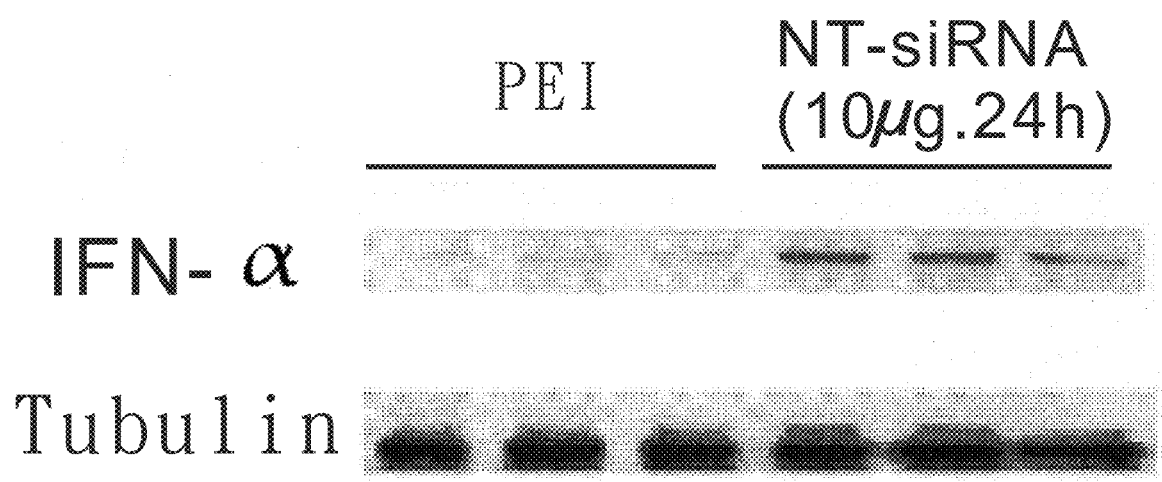
FIG. 2 is a western blot datum illustrating SD rats' protein expression in each group.

FIG. 2 shows a western blot data of L4-L5 spinal cord segments of the SD rats in the said two groups, wherein the SD rats are killed by decapitation under deep anesthesia.

Specifically, for western blotting, the SD rats are killed by decapitation under deep anesthesia (by intraperitoneal injecting pentobarbital in a dosage of 120 mg/kg), next, the L4-L5 spinal cord segments are quickly removed from the SD rats and homogenized with a hand-held pellet pestle in TPER Tissue Protein Extraction Reagent (Pierce, Rockford, Ill., USA) [25 mM bicine, 150 mM sodium chloride (pH 7.6)] containing protease inhibitors (Protease Inhibitor Cocktail, Calbiochem, Darmstadt, Germany) [100 mM 4-(2-aminoethyl)benzenesulfonyl fluoride hydrochloride, 80 μM aprotinin, crystalline, 5 mM bestatin, 1.5 mM E-64 protease inhibitor, 2 mM leupeptin, and 1 mM pepstatin A], and then, placed on ice for 30 min and centrifuged at 10,000 g for 15 min at 4° C. to take supernatant. As following, the supernatant is collected, assayed for protein content via Bio-Rad DC Protein Assay Kit (Bio-Rad Laboratories, Hercules, Calif., USA), and stored at −20° C. until further use.

In western blotting, 30 μg protein samples (being prepared according to procedures of above paragraph) of the SD rats of the said two groups are boiled under denaturing conditions for 10 min, separated on sodium dodecyl sulphate-polyacrylamide gel electrophoresis gels (5-10% gradient gel) with running buffer and molecular weight standards as suggested by the manufacturer, and further transferred to polyvinylidene difluoride membranes (Immobilon-P, Millipore, Bedford, Mass., USA). After that, the polyvinylidene difluoride membranes are blocked with 5% nonfat milk in phosphate-buffered saline (PBS) for one hour, sequentially incubated overnight at 4° C. with polyclonal antibody against IFN-α (in a titer of 1:500, R & D Systems Inc., NC, USA) and mouse monoclonal anti-β-tubulin (in a titer of 1:2000, Santa Cruz Biochemicals, Inc., Santa Cruz, Calif., USA) being diluted in 0.1% Tween 20-PBS, washed in a washing buffer for 30 min at room temperature, and incubated in horseradish peroxidase-conjugated donkey anti-goat immunoglobulin G (being diluted to 1:5000 in 5% milk-PBS; Jackson ImmunoResearch, West Grove, Pa., USA) and horseradish peroxidase-linked sheep anti-mouse IgG (being diluted to 1:5000 in 5% milk-PBS; Amersham Biosciences, Arlington Heights, Ill., USA) for one hour at room temperature.

Finally, for visualization, the polyvinylidene difluoride membranes are incubated with chemiluminescent solution (Immobilon Western Chemiluminescent HRP Substrate; Millipore, Billerica, Mass., USA), washed in a washing buffer for another 30 min, and visualized on an UVP BioSpectrum 500 Imaging System (UVP, Upland, Calif., USA).

Figure 3:
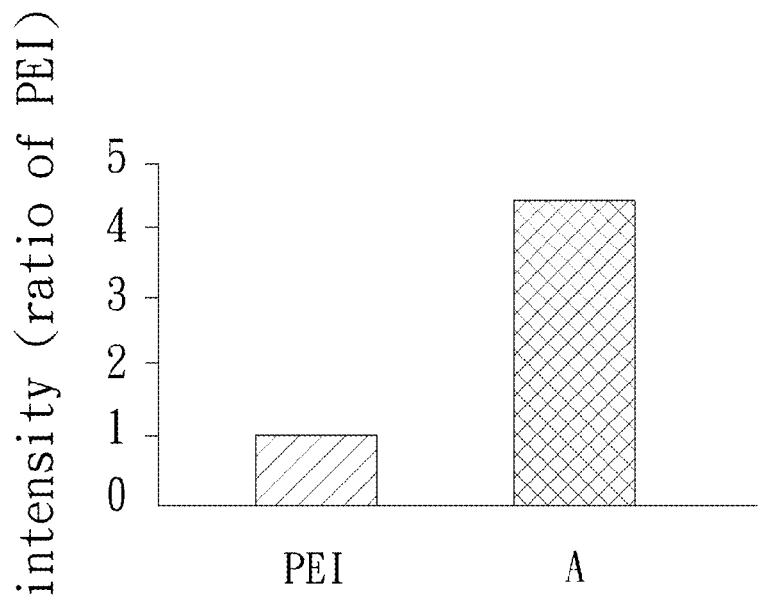
FIG. 3 is a bar chart illustrating ratio of interferon-α in SD rats of each group.

In FIG. 2, it is noted that, levels of interferon-α in spinal cord are significantly increased after intrathecal delivery of the analgesic medication of the present invention. Furthermore, FIG. 3 shows a ratio of levels of interferon-α in the SD rats of the two groups, and it is pointed out that, four times of interferon-α is observed in the SD rats that had intrathecal delivery of the analgesic medication of the present invention, in comparison with the SD rats that had the PEI injection only.

Therefore, with the above-defined experiments, it is believed that the analgesic medication of the present invention that delivered intrathecally indeed has ability of inducing interferon-α response in individuals, and further achieving reversible anti-allodynia in central nervous systems, with slightly response of stimulus-induced heat hypersensitivity and allodynia being observed on the individuals.

Figure 4:
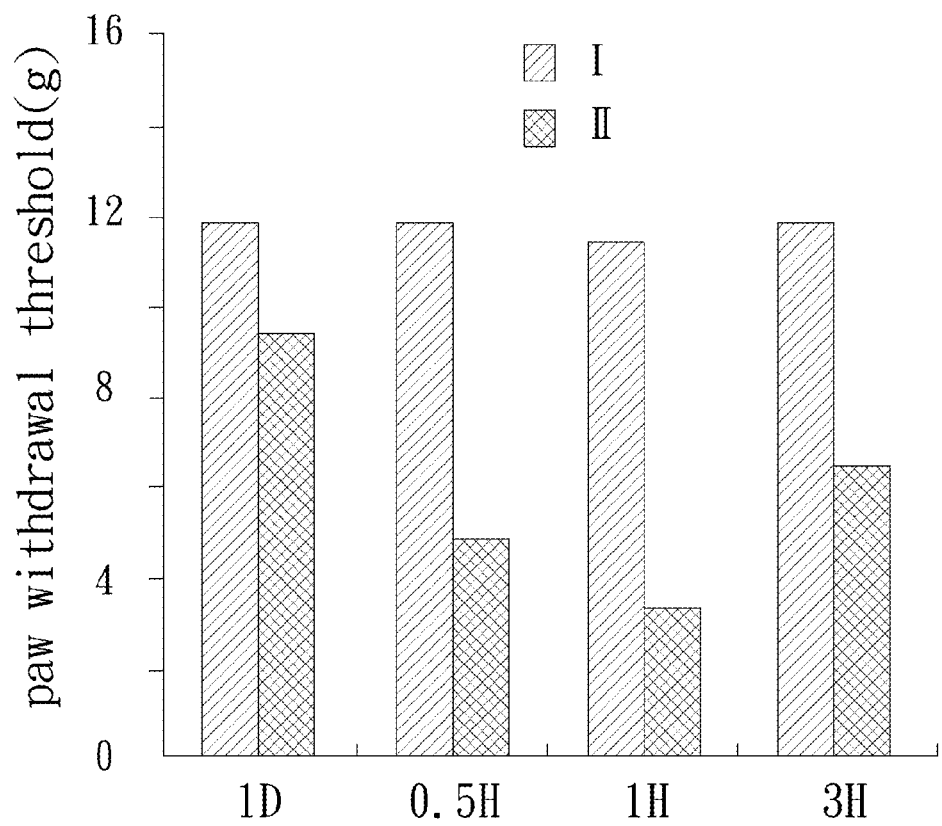
FIG. 4 is a bar chart illustrating paw withdrawal threshold of rats in each group.

With reference to FIG. 4, the other two groups of SD rats are prepared and carried out two injections, with a first injection thereof being performed by intrathecally injecting 40 μl the saline or a mixture comprising 10 μg the oligonucleotide A, the PEI solution and an interferon-α neutralizing antibody, and with a second injection thereof being performed by subcutaneously injecting 100 μl CFA on a hind paw of the SD rats of each group (as summarize in TABLE 3). Then, mechanical allodynia is tested in half (0.5H), one (1H), three (3H), and twenty-four hours (1 D) after the second injection.

TABLE 3

Assignments of SD rats in the other Two Groups

| | First Injection | | Second Injection | |
| --- | --- | --- | --- | --- |
| Groups | Injection | Dosage | Injection | Dosage |
| I | saline | 40 μl | CFA | 100 μl |
| II | A[a] + PEI | 10 μg | CFA | 100 μl |
| | interferon-α neutralizing antibody | 30 ng | | |

[a]Per microgram of the oligonucleotide is mixed with 0.18 μl the PEI solution

IN FIG. 4, it is shown that the interferon-α induced anti-allodynic effect that is conducted by delivered analgesic medication is reversed by intrathecal administration of interferon-α neutralizing antibody. Thus, it is proved that the anti-allodynic effect that is induced by the analgesic medication is directly related to interferon-α response.

In TABLE 4, the SD rats are randomly assigned to four groups including i, ii, iii, and iv, and carried out two injections, with a first injection thereof being performed by intrathecally injecting 100 ng interferon-α, 100 ng interferon-α and 20 nmole naloxone, 10 μg the oligonucleotide A and the PEI solution, and a mixture comprising 10 μg the oligonucleotide A, the PEI solution and 20 nmole naloxone to the SD rats in the four groups respectively, and with a second injection thereof being performed one day after by subcutaneously injecting 100 μl CFA on a hind paw of the SD rats of each group. After that, mechanical allodynia of the SD rats in each group is tested in half (0.5H), one (1H), two (2H), and four (4H) and twenty-four hours (1 D) after the second injection.

TABLE 5

Assignments of SD Rats in the Four Groups

| Groups | First Injection | | Second Injection |
|---|---|---|---|
| | Injection | Dosage | Injection |
| i | IFN-α | 100 ng | CFA 100 μl |
| ii | IFN-α naloxone | 100 ng 20 nmole | CFA 100 μl |
| iii | $A^a$ + PEI | 10 μg | CFA 100 μl |
| iv | $A^a$ + PEI naloxone | 10 μg 20 nmole | CFA 100 μl |

$^a$Per microgram of the oligonucleotide is mixed with 0.18 μl the PEI solution

Figure 5:
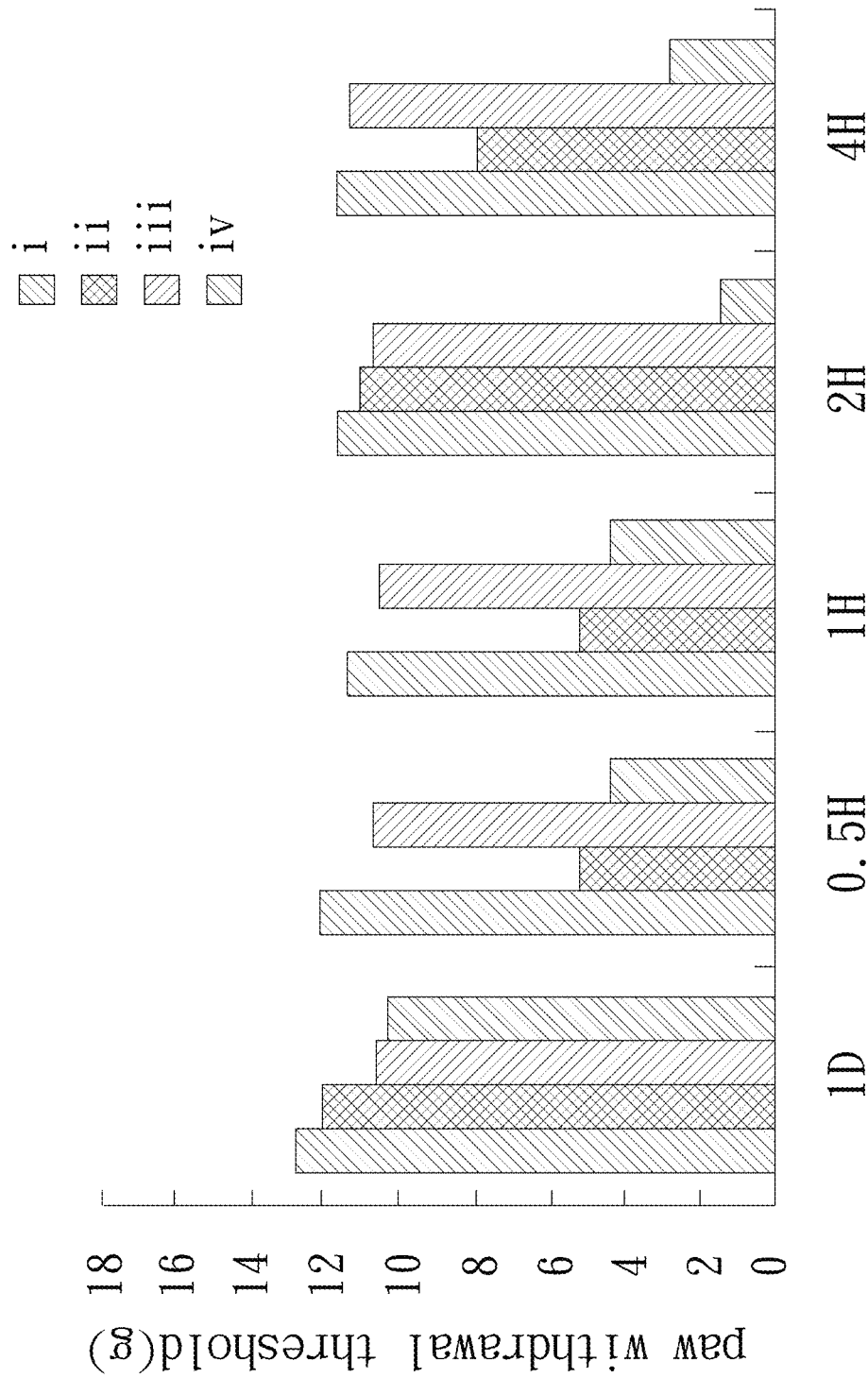
FIG. 5 is another bar chart illustrating paw withdrawal threshold of rats in each group.

FIG. 5 indicates that intrathecal administration of an opioid receptor antagonist-naloxone (20 nmole) reverses the analgesic effects induced by the analgesic medication of the present invention, and therefore, it is further demonstrated that the analgesic medication of the present invention will produce pain relief by inducing interferon-α response through activate spinal opioid receptors.

According to above-defined two experiments, it is believed that, the olignonucleotide in the analgesic medication that delivered intrathecally will induce interferon-α response in individuals to achieve reversible analgesic effect in central nervous systems via activating spinal opioid receptors, and thus that stimulus-induced heat hypersensitivity and allodynia that is observed on the individuals will be significantly relieved.

In summary, the analgesic medication is provided, comprising the olignocleotide, being apt to induce interferon-α response in individuals and to achieve reversible analgesic effect in central nervous systems without leading to side effects caused by directly delivery of interferon-α; and a pharmaceutical acceptable vehicle for delivering the said oligonucleotide into cells (such as PEI). With the combination of the PEI, the olignocleotide in the analgesic medication can be successfully delivered to the cells in central nervous system to produce reversible analgesic effects in central nervous systems, and therefore, the analgesic medication of the present invention is capable of being applied to clinical medicine for systemic analgesia.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A method of analgesia comprising inducing interferon-α response and thereby achieving reversible analgesic effects in an individual's central or peripheral nervous system via activation of μ-opioid receptors by administrating an analgesic medication to the individual via intrathecal injection, wherein the analgesic medication comprises an oligonucleotide being a double strand RNA comprising sequence set forth in SEQ ID NOs: 1 and 2 and a pharmaceutical acceptable vehicle, for delivering the said oligonucleotide into cells, wherein a dosage of the oligonucleotide in the analgesic medication is 50 μg to 200 μg/per kg/per time.

2. The method of analgesia as defined in claim 1, wherein the individual is human body or rat.

3. The method of analgesia as defined in claim 1, wherein the analgesic medication is used for systemic analgesia or pain relief.

4. The method of analgesia as defined in claim 3, wherein the analgesic medication is used for local analgesia on lumbar vertebra, extremity or lower body.

5. A method of analgesia comprising inducing interferon-α response and thereby achieving reversible analgesic effects in an individual's central or peripheral nervous system via activation of μ-opioid receptors by administrating an analgesic medication to the individual via intrathecal injection, wherein the analgesic medication comprises an oligonucleotide being a double strand RNA comprising sequence set forth in SEQ ID NOs: 3 and 4 and a pharmaceutical acceptable vehicle, for delivering the said oligonucleotide into cells, wherein a dosage of the oligonucleotide in the analgesic medication is 50 μg to 200 μg/per kg/per time.

6. The method of analgesia as defined in claim 1, wherein the oligonucleotide and the pharmaceutical acceptable vehicle are mixed in a ratio of 1 μg:0.18 μl.

7. The method of analgesia as defined in claim 1, with the oligonucleotide being small interfering RNA, short hairpin RNA, or microRNA.

8. The method of analgesia as defined in claim 1, wherein the pharmaceutical acceptable vehicle is selected from a group of polyethyleneimine, lipofectamine and iFect.

9. The method of analgesia as defined in claim 5, wherein the individual is human body or rat.

10. The method of analgesia as defined in claim 5, wherein the analgesic medication is used for systemic analgesia or pain relief.

11. The method of analgesia as defined in claim 5, wherein the analgesic medication is used for local analgesia on lumbar vertebra, extremity or lower body.

12. The method of analgesia as defined in claim 5, wherein the oligonucleotide and the pharmaceutical acceptable vehicle are mixed in a ratio of 1 μg:0.18 μl.

13. The method of analgesia as defined in claim 5, with the oligonucleotide being small interfering RNA, short hairpin RNA, or microRNA.

14. The method of analgesia as defined in claim 5, wherein the pharmaceutical acceptable vehicle is selected from a group of polyethyleneimine, lipofectamine and iFect.

* * * * *